US011473126B2

(12) United States Patent
Lee et al.

(10) Patent No.: US 11,473,126 B2
(45) Date of Patent: Oct. 18, 2022

(54) METHOD FOR ANALYZING MELTING CURVE USING BI-FUNCTIONAL PNA PROBE, METHOD FOR DIAGNOSING MICROSATELLITE INSTABILITY USING THE SAME, AND KIT FOR DIAGNOSING MICROSATELLITE INSTABILITY

(71) Applicant: SEASUNBIO MATERIALS, Daejeon (KR)

(72) Inventors: Han Woo Lee, Daejeon (KR); Si Seok Lee, Daejeon (KR); Deokhwe Hur, Daejeon (KR); Hee Kyung Park, Daejeon (KR)

(73) Assignee: SEASUNBIO MATERIALS, Daejeon (KR)

( * ) Notice: Subject to any disclaimer, the term of this patent is extended or adjusted under 35 U.S.C. 154(b) by 338 days.

(21) Appl. No.: 16/488,588

(22) PCT Filed: Mar. 24, 2017

(86) PCT No.: PCT/KR2017/003168
§ 371 (c)(1),
(2) Date: Aug. 25, 2019

(87) PCT Pub. No.: WO2018/174318
PCT Pub. Date: Sep. 27, 2018

(65) Prior Publication Data
US 2020/0248240 A1 Aug. 6, 2020

(30) Foreign Application Priority Data
Mar. 24, 2017 (KR) .................. 10-2017-0037506

(51) Int. Cl.
*C12Q 1/6818* (2018.01)
*C12Q 1/6886* (2018.01)

(52) U.S. Cl.
CPC ......... *C12Q 1/6818* (2013.01); *C12Q 1/6886* (2013.01); *C12Q 2600/156* (2013.01)

(58) Field of Classification Search
None
See application file for complete search history.

(56) References Cited

U.S. PATENT DOCUMENTS 6,664,064 B1 * 12/2003 Dietmaier ............ C12Q 1/6827
435/6.11
2003/0113723 A1 6/2003 Bapat et al.

FOREIGN PATENT DOCUMENTS

| CN | 102230004 B | * | 12/2012 |
| JP | 2008507976 A | | 3/2008 |
| KR | 20020086078 A | | 11/2002 |
| KR | 100998272 A | | 12/2010 |
| KR | 100998272 B1 | | 12/2010 |
| KR | 20140046688 A | | 4/2014 |

OTHER PUBLICATIONS

Hur et al Biological procedures Online. 2015. 17:14 (Year: 2015).*
Boland, C.R., et al., "A National Cancer Institue Workshop on Microsatellite Instability for Cancer Detection and Familial Predisposition: Development of International Criteria for the Determination of Microsatellite Instability in Colorectal Cancer", "Cancer Research", Nov. 15, 1998, pp. 5248-5257, vol. 58.
Buhard, O., et al., "Quasimonomorphic Mononucleotide Repeats for High-Level Microsatellite Instability Analysis", "Disease Markers", 2004, pp. 251-257, vol. 20.
Church, D.N., et al., "DNA Polymerase epsilon and delta Exonuclease Domain Mutations in Endometrial Cancer", "Human Molecular Genetics", 2013, pp. 2820-2828, vol. 22, No. 14.
Cristescu, R., et al., "Molecular Analysis of Gastric Cancer Identifies Subtypes Associated With Distrinct Clinical Outcomes", "Nature Medicine", 2015, pp. 1-10.
Deschoolmeester, V., et al., "Detection of Microsatellite Instability in Colorectal Cancer Using an Alternative Multiplex Assay of Quasi-Monomorphic Mononucleotide Markers", "Journal of Molecular Diagnostics", 2008, pp. 154-159, vol. 10, No. 2.
Goel, A., et al., "An Optimized Pentaplex PCR for Detecting DNA Mismatch Repair-Deficient Colorectal Cancers", "PLOS One", Feb. 2010, p. e9393: 1-9, vol. 5, No. 2.
Kim, D., "Hereditary Colorectal Cancer", "Journal of Genetic Medicine", 2010, pp. 24-36.

(Continued)

*Primary Examiner* — Carla J Myers
(74) *Attorney, Agent, or Firm* — Hultquist, PLLC; Steven J. Hultquist

(57) ABSTRACT

Disclosed are a method for analyzing a melting curve using bi-functional fluorescent PNA probes, a method for diagnosing microsatellite instability (MSI) using the same, and a kit for diagnosing microsatellite instability (MSI) using the same. More particularly, disclosed are a method for analyzing a melting curve, based on the structure of fluorescent PNA probes that bind with different binding forces depending on the number of base mutations deleted using the fluorescent PNA probes capable of specifically binding to regions where the same base is repeated, and a method for rapidly and accurately detecting and analyzing microsatellite instability (MSI) by detecting gene mutation of microsatellite markers caused by base deletion in regions where the same base is repeated using the analysis method and analyzing the number of base mutations thus obtained. The method and kit can analyze the presence of deletion of microsatellite marker genes with high sensitivity and specificity using five microsatellite markers of Quasi loci, thus having advantages of reducing costs, shortening a test time, and the like, as compared to conventional MSI diagnostic methods.

7 Claims, 6 Drawing Sheets

Specification includes a Sequence Listing.

(56) References Cited

OTHER PUBLICATIONS

Le, D.T., et al., "PD-1 Blockade in Tumors with Mismatch-Repair Deficiency", "The New England Journal of Medicine", 2015, pp. 1-12.

Palmieri, C., et al., "Genetic Instability and Increased Mutational Load: Which Diagnostic Tool Best Direct Patients With Cancer to Immunotherapy?", "Journal of Translational Medicine", 2017, pp. 1-4, vol. 15, No. 17.

Viana-Pereira, M., et al., "Analysis of Microsatellite Instability in Medulloblastoma", "Neuro-Oncology", 2009, pp. 458-467.

* cited by examiner

METHOD FOR ANALYZING MELTING CURVE USING BI-FUNCTIONAL PNA PROBE, METHOD FOR DIAGNOSING MICROSATELLITE INSTABILITY USING THE SAME, AND KIT FOR DIAGNOSING MICROSATELLITE INSTABILITY

CROSS-REFERENCE TO RELATED APPLICATIONS

This application is a U.S. national phase under the provisions of 35 U.S.C. § 371 of International Patent Application No. PCT/KR17/03168 filed Mar. 24, 2017, which in turn claims priority under 35 U.S.C. § 119 of Korean Patent Application No. 10-2017-0037506 filed Mar. 24, 2017. The disclosures of International Patent Application No. PCT/KR17/03168 and Korean Patent Application No. 10-2017-0037506 are hereby incorporated herein by reference, in their respective entireties, for all purposes.

TECHNICAL FIELD

The present invention relates to a method for analyzing a melting curve using bi-functional fluorescent PNA probes, a method for diagnosing microsatellite instability (MSI) using the same, and a kit for diagnosing microsatellite instability (MSI) using the same. More particularly, the present invention relates to a method for analyzing a melting curve, based on the structure of fluorescent PNA probes that bind with different binding forces depending on the number of base mutations deleted using the fluorescent PNA probes capable of specifically binding to regions where the same base is repeated, and a method for rapidly and accurately detecting and analyzing microsatellite instability (MSI) by detecting gene mutation of microsatellite markers caused by base deletion in regions where the same base is repeated using the analysis method and analyzing the number of base mutations thus obtained.

BACKGROUND ART

Microsatellites refer to tracks of repetitive genetic sequences in which six or fewer short DNA base sequences are sequentially repeatedly arranged throughout the human genome. These are distributed with different repetitions on respective chromosomes.

Microsatellite instability (MSI) refers to variability in length that is caused by increase or decrease of short tandem repeat sequences constituting microsatellites, which undergoes the recovery process by mismatch repair genes (MMR genes). However, recovery abnormality, which results from promotor methylation, germline mutation of DNA mismatch repair (MMR) genes or the like, may change the length of microsatellites. Gene repair abnormality can be diagnosed by detection of such microsatellite instability. Such MSI was first found in patients with hereditary nonpolyposis colorectal cancer (HNPCC) syndrome. It was reported that about 90% of HNPCC patients have the MSI. Further, MSI is found in a variety of other tumors, in particular, MSI (+) is expressed at a high incidence of 75% or more in endometrial cancer, which the most generally occurs in patients with hereditary nonpolyposis colorectal cancer syndrome. MSI (+) is found to be present in sporadic colorectal cancer and sporadic endometrial cancer having no family history of hereditary nonpolyposis colorectal cancer (HNPCC) and the like. In particular, for example, it was variably reported that the incidence of MSI (+) in sporadic endometrial cancer reaches about 10 to 40% in other countries and the incidence of MSI (+) in sporadic endometrial carcinoma reaches about 20 to 24% in Korea. Recently, it has been reported that MSI-type colon and stomach cancer patients have good prognosis for immunotherapy, and thus there is an increasing need for a microsatellite instability test as a biomarker of immunotherapeutic agents (Le et al., *N Engl J Med.* 372.26: 2509-2520, 2015; Cristescu et al., *Nature Medicine* 21.5: 449-456, 2015).

According to international standards, MSI is generally classified into two types. The National Cancer Institute (NCI), in 1997, suggested five microsatellite markers (BAT-25, BAT-26, D2S123, D17S250, and D5S346) including two mononucleotide repeat microsatellites and three dinucleotide repeat microsatellites. The case where two or more of the markers show instability corresponds to high-level MSI (MSI-H) wherein 40% or more of the microsatellite markers have microsatellite instability, which is also called "replication error positive (RER+)". The case where only one marker shows instability corresponds to low-level MSI (MSI-L) wherein 40% or less of the microsatellite markers have microsatellite instability. The case where there is no microsatellite instability is defined as microsatellite stability (MSS). (Boland et al., *Cancer Res.*, 58:5248-57, 1998; Kim, Duekwoo, *Journal of Genetic Medicine* 7:24-36, 2010).

The method for diagnosing MSI which has been generally used to date is diagnosis by analysis of the length distribution of products amplified from markers by polymerase chain reaction using capillary electrophoresis. In particular, the analysis method of "Multiplex fluorescence PCR amplification and capillary electrophoresis", which is the most widely known, is a method of analyzing MSI by extracting DNAs from normal tissues and tumor tissues, amplifying the DNAs through fluorescent polymerase chain reaction that targets the five microsatellite markers recommended by the National Cancer Institute (US), and then analyzing the fluorescence expressed by fluorescently labeled DNAs using capillary electrophoresis. However, this requires a costly capillary electrophoresis apparatus, entails inconvenience associated with the two-step process including DNA amplification through fluorescent polymerase chain reaction, followed by subjecting DNAs to capillary electrophoresis, and takes at least seven days to complete the test. In addition, the use of dinucleotide repeat markers may be considered because there the use of mononucleotide repeat markers has a limitation due to low resolution of electrophoresis. However, there is a limitation wherein the sensitivity and specificity of D2S123, D17S250 and D5S346, three biomarkers composed of dinucleotides, among the five microsatellite biomarkers recommended by the US National Cancer Institute, are considerably low, as compared to those of BAT25 and BAT26, two biomarkers composed of mononucleotides. In addition, although the MSI test is performed separately on normal tissues and cancer tissues, the cancer tissues have cell-to-cell heterogeneity as well, thus disadvantageously making it difficult to test MSI present at a low rate of less than 10% with the current diagnosis method.

In recent years, there has been an increasing need for selection of highly sensitive markers and diagnostic technologies for the markers. Recently, quasi loci (BAT25, BAT26, NR21, NR24 and NR27) selected through the statistical database have been used, rather than Bethesda loci (BAT25, BAT26, D2S123, D17S250 and D5S346) which were first used by the national cancer institute and have generally been used since then. In MSI analysis, Quasi loci are more sensitive and accurate than conventional Bethesda loci (Buhard et al., *Disease Markers*, 20:251-7, 2004;

Deschoolmeester et al., *J Mol Diagn*, 10:154-159, 2008). Quasi loci are markers in which mononucleotides are repeated. Since a small number of base deletions should be analyzed for analysis of the corresponding markers, analysis resolution needs to be improved for accurate determination.

In recent years, technologies capable of effectively detecting single base mutations of target nucleic acids, and mutations of bases by deletion or insertion through melting curve analysis using peptide nucleic acid (PNA) probes including reporters and quenchers coupled thereto are receiving a great deal of attention. Since PNAs are more thermally and biologically stable than DNAs and have better abilities to recognize and bind to target DNAs, PNA probes can bind to the target DNAs faster and stronger than DNA probes. Due to the strong bonding, shorter length of PNA probes can be used, thus it has an advantage of detecting single base sequence mutations that are adjacent to each other. On the other hand, it has a limitation that this melting curve analysis can be used only to a simple distinguish of single base mutation and base mutation by deletion or insertion from normal target nucleic acids through comparison. In addition, the PNA probes can function to inhibit the polymerase elongation reaction when maintaining the binding in the polymerase elongation reaction step during polymerase chain reaction, and is capable of preferentially amplifying the desired single base mutation using the inhibitory effect and the change in the binding force due to the difference in the single base mutations.

Under these technical backgrounds, as a result of intensive efforts to develop a diagnostic method and kit for microsatellite instability (MSI) based on analysis of the number of deleted base mutations through melting curve analysis using PNA probes that are coupled to reporters and quenchers and have a higher complementary binding temperature to normal sequences than the elongation (extension) reaction temperature of polymerase chain reaction, the present inventors have found that the presence of base deletion can be detected with a high sensitivity and specificity through melting curve analysis, based on the structure to bind specifically to the base deletion of the target nucleic acid, using PNA probes that are designed to be coupled to reporters and quenchers, to have a higher binding temperature to normal sequences than the polymerase elongation (extension) reaction temperature, and to have a lower binding temperature to sequences with one or more deletions than the polymerase elongation (extension) reaction temperature, and even that base deletion of Quasi loci microsatellite markers present at a low rate of about 5% can be detected based on this method, thus eventually completing the present invention.

DISCLOSURE

Technical Problem

Therefore, the present invention has been made in view of the above problems, and it is one object of the present invention to provide a method and kit for diagnosing microsatellite instability (MSI) with high sensitivity using a bifunctional peptide nucleic acid (PNA) probe that has a reporter and a quencher coupled thereto and is selected from the group consisting of the sequences having SEQ ID NOS: 11 to 23.

Technical Solution

In accordance with the present invention, the above and other objects can be accomplished by the provision of a method of analyzing a melting curve for diagnosis of microsatellite instability (MSI) based on detection of base mutations of a microsatellite target nucleic acid using a PNA (peptide nucleic acid) probe selected from the group consisting of sequences having SEQ ID NOS: 11 to 23 and sequences complementary thereto, wherein the PNA probe has a reporter and a quencher coupled thereto.

In accordance with another aspect, provided is a method for diagnosing microsatellite instability (MSI), based on detection of base mutations of a target nucleic acid comprising:

(a) purifying the target nucleic acid from a test sample, and mixing the target nucleic acid with a PNA probe selected from the group consisting of sequences having SEQ ID NOS: 11 to 23 and sequences complementary thereto, to hybridize the PNA probe with the target nucleic acid;

(b) denaturating the hybridized product, while changing a temperature, to obtain a melting curve; and (c) analyzing the obtained melting curve to detect a presence of base mutations in a microsatellite marker present in the target nucleic acid and the number of the base mutations, wherein the target nucleic acid comprises BAT25, BAT26, NR21, NR24 or NR27 as the microsatellite marker.

In accordance with another aspect, provided is a kit for diagnosis of microsatellite instability (MSI) based on detection of base mutations of a target nucleic acid using melting curve analysis, comprising i) a PNA (peptide nucleic acid) probe having a reporter and a quencher coupled thereto, and selected from the group consisting of sequences having SEQ ID NOS: 11 to 23 and sequences complementary thereto, and ii) a primer set selected from the group consisting of: SEQ ID NO: 1 and SEQ ID NO: 2; SEQ ID NO: 3 and SEQ ID NO: 4; SEQ ID NO: 5 and SEQ ID NO: 6; SEQ ID NO: 7 and SEQ ID NO: 8; and SEQ ID NO: 9 and SEQ ID NO: 10.

In accordance with another aspect, provided is a kit for detecting malfunction of genes involved in DNA mismatch repair based on detection of base mutations of a microsatellite target nucleic acid using a PNA (peptide nucleic acid) probe having a reporter and a quencher coupled thereto, and selected from the group consisting of sequences having SEQ ID NOS: 11 to 23 and sequences complementary thereto.

In accordance with another aspect, provided is a kit for detecting malfunction of genes involved in DNA proofreading based on detection of base mutations of a microsatellite target nucleic acid using a PNA (peptide nucleic acid) probe having a reporter and a quencher coupled thereto, and selected from the group consisting of sequences having SEQ ID NOS: 11 to 23 and sequences complementary thereto.

In accordance with yet another aspect, provided is a kit for detecting mutations caused by malfunction of DNA mismatch repair or DNA proofreading using a PNA (peptide nucleic acid) probe having a reporter and a quencher coupled thereto, and selected from the group consisting of sequences having SEQ ID NOS: 11 to 23 and sequences complementary thereto.

DETAILED DESCRIPTION OF THE INVENTION AND SPECIFIC EMBODIMENTS

Unless defined otherwise, all technical and scientific terms used herein have the same meaning as those appreciated by those skilled in the field to which the present invention pertains. In general, nomenclature used herein is well-known in the art and is ordinarily used.

The present invention relates to a method for testing microsatellite instability (MSI) with high sensitivity by identifying the presence of microsatellite deletion through amplification of markers with high sensitivity and melting curve analysis using peptide nucleic acid (PNA) probes that have a reporter and a quencher coupled thereto and are capable of selectively (preferentially) amplifying markers having microsatellite instability (MSI).

Five microsatellite markers of Quasi loci (NR21, NR24, BAT26, NR27 and BAT25) were selected as markers for testing microscopic instability according to the present invention, and a set of fluorescent PNA probes for determining whether or not the markers are deleted include one or more of SEQ ID NO: 11, SEQ ID NO: 12 and SEQ ID NO: 13 of NR21, and one or more of SEQ ID NO: 14, SEQ ID NO: 15 and SEQ ID NO: 16 of NR24, SEQ ID NO: 17 of BAT26, one or more of SEQ ID NO: 18, SEQ ID NO: 19, SEQ ID NO: 20 and SEQ ID NO: 21 of BAT25, and one or more of SEQ ID NO: 22 and SEQ ID NO: 23 of NR27.

Figure 4:
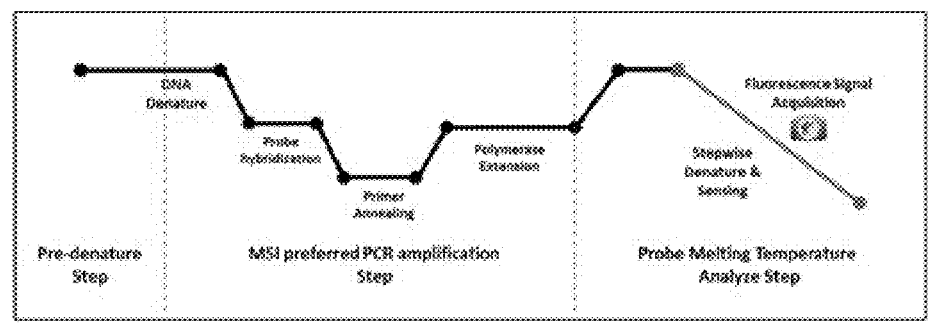
FIG. 4 is a schematic diagram illustrating real-time PCR reaction conditions to identify the presence of microsatellite deletion.

In one embodiment of the present invention, bifunctional fluorescent PNA probes were produced and screened for the diagnosis of microsatellite markers (see FIG. 4). The bifunctional PNA probes are fluorescently conjugated PNA probes, which are designed to have both a function of inhibiting the elongation reaction of the polymerase when maintaining complete binding with the complementary sequence and a function of analyzing fluorescence. The bifunctional PNA probes are designed to have a higher binding temperature to normal sequences than the elongation reaction temperature of the polymerase so as to provide amplification preferred (specific) for microsatellite instability (deletion), and to have a lower binding temperature to microsatellite markers containing deletion sequences than the elongation reaction temperature of the polymerase. The bifunctional PNA probes were selected using the sequences of SEQ ID NOS: 11 to 23 so that these characteristics can be imparted thereto.

Preferably, in the PNA probe according to the present invention, the binding force (melting temperature, Tm) between the PNA probe and the microsatellite marker sequence is determined by controlling the base sequence of the probe and the length thereof. Specifically, examples of other methods include reducing the binding force through substitution of a part of sequence and controlling the binding force through deformation of the backbone of PNA monomers.

The substitution of the sequence part may be performed using a sequence part containing a base that is not complementary to a target, and may be performed using one or more selected from the group consisting of inosine PNA, indole PNA, nitroindole PNA and an abasic, which are bases that bind to a natural base such as adenine, guanine, cytosine, thymine or uracil without selectivity, and have a lower binding force than complementary bonding force. In addition, the method of controlling the binding force through deformation of the backbone of PNA monomers may include incorporation of gamma- or alpha-backbone modified PNA monomers. In particular, examples thereof include the use of gamma- or alpha-backbone modified peptide nucleic acid monomers including, in the backbone thereof, amino acids having one or more positive charges selected from the group consisting of lysine (Lys, K), arginine (Arg, R), histidine (His, H), diamino butyric acid (DAB), ornithine (Orn) and amino acid analogs, which are positively charged to improve the binding force, and gamma- or alpha-backbone modified PNA monomers including, in the backbone thereof, amino acids such as glutamic acid (Glu, E) and aspartic acid (Asp, D), which are negatively charged to improve the binding force, and modified PNAs which affect the binding force between PNA such as alanine (Ala, A) and the target.

Accordingly, in one aspect, the present invention provides method of analyzing a melting curve for diagnosis of microsatellite instability (MSI) based on detection of base mutations of a microsatellite target nucleic acid using a PNA (peptide nucleic acid) probe selected from the group consisting of sequences having SEQ ID NOS: 11 to 23 and sequences complementary thereto, wherein the PNA probe has a reporter and a quencher coupled thereto.

As used herein, the term "base variation (mutation)" refers to a phenomenon in which a base sequence of a target nucleic acid is mutated and includes not only a single nucleotide polymorphism (SNP) but also mutation of a base by substitution, deletion or insertion. Preferably, the PNA probes according to the present invention can be used to analyze mutation caused by deletion of 2 to 14 bases of the target nucleic acid through melting curve analysis.

In the present invention, the melting curve analysis may be performed by fluorescence melting curve analysis (FMCA) and the amplification may be performed by real-time polymerase chain reaction (PCR).

As used herein, the term "hybridization" means that complementary single-stranded nucleic acids form double-stranded nucleic acids. Hybridization may occur either in perfect match in which complementarity between two nucleic acid strands is perfect, or even in the presence of some mismatch bases. The degree of complementarity required for hybridization may vary depending on the hybridization conditions and, in particular, can be controlled by temperature.

The fluorescent peptide nucleic acid probe containing a reporter and a quencher according to the present invention is hybridized with the target nucleic acid, and then generates a fluorescence signal. As temperature rises, the probe rapidly melts with the target nucleic acid at a suitable melting temperature of the probe, causing the fluorescence signal to be quenched. Whether or not base variation (SNP, Indel or the like) of the target nucleic acid occurs can be detected through high-resolution fluorescence melting curve analysis (FMCA) obtained from the fluorescence signal according to temperature change.

As used herein, the term "target nucleic acid" refers to a nucleic acid sequence (including SNP) of a genotype to be detected/discriminated, includes a specific region of a nucleic acid sequence of a "target gene" encoding a protein having a physiological and/or biochemical function, and is annealed or hybridized with a primer or probe under hybridization, annealing or amplification conditions. The target nucleic acid is not different from the term "target nucleic acid", "synthetic DNA" or "artificially synthetic oligo" as used herein, and is used interchangeably herein.

In the present invention, the target nucleic acid is DNA or RNA, and the molecule may be a double-stranded or single-stranded form. When the nucleic acid as the starting material is double stranded, it is preferable to produce the two strands into a single strand or partially single-strand. Known methods to separate strands include, but are not limited to, heat, alkaline, formamide, urea and glyoxal treatment, enzymatic methods (helicase action), and binding proteins. For example, the strand separation can be carried out by heat treatment at a temperature of 80 to 105° C. A general method of the treatment as described above is disclosed in Joseph Sambrook et al., Molecular Cloning, 2001.

The fluorescent PNA probe according to the present invention is preferably designed such that base mutation of the target nucleic acid is located at the center position of the fluorescent PNA probe to induce a difference in melting temperature (Tm) between target nucleic acid and base mutation-containing target nucleic acid. When the base mutation region is located at the center of the probe, a structural difference of the probe is created, and the fluorescent PNA probe joins while forming a loop, and the difference in the melting temperature (Tm) is thus great due to such a structural difference.

According to the present invention, the PNA probe may be designed such that a binding force in perfect match (hybridization) between the PNA probe and a target microsatellite sequence is higher than a polymerase elongation reaction temperature and a binding force in mismatch (hybridization with at least one deletion) between the PNA probe and a target microsatellite sequence is lower than the polymerase elongation reaction temperature.

In the present invention, the fluorescent PNA probe performs analysis using a hybridization method different from the hydrolysis method of the TaqMan probe, and examples of the probe having a similar function thereto include molecular beacon probes, scorpion probes and the like.

In the present invention, the fluorescent PNA probe preferably has a reporter and a quencher at both ends thereof. That is, the reporter and the quencher capable of quenching the reporter fluorescence may be combined at both ends of the PNA probe according to the present invention. The reporter may include one or more selected from the group consisting of FAM (6-carboxyfluorescein), Texas red, HEX (2',4',5',7',-tetrachloro-6-carboxy-4,7-dichlorofluorescein) and CY5, and the quencher may include one or more selected from the group consisting of TAMRA (6-carboxytetramethyl-rhodamine), BHQ1, BHQ2 and Dabcyl, but is not limited thereto. Preferably, Dabcyl is used.

In the present invention, the PNA probe has an expected melting temperature (Tm) when forming perfect match with the microsatellite target nucleic acid, and the PNA probe has a lower melting temperature (Tm) than the expected melting temperature (Tm) when forming mismatch with the microsatellite target nucleic acid having at least one base mutation.

In another embodiment of the present invention, it was identified that single or multiple analysis as to whether or not deletion of the microsatellite marker occurs was possible using standard cell lines (Table 3) of microsatellite instability (MSI) status and microsatellite stability (MSS) status, in order to analyze microsatellite instability (MSI) and microsatellite stability (MSS) using five microsatellite markers of quasi-loci with high sensitivity and specificity.

Bifunctional PNA probes function to inhibit the polymerase chain reaction of normal microsatellite markers, while allowing for polymerase chain reaction of microsatellite markers with one or more deletions, thus having high analytical sensitivity. Such sensitivity was confirmed through Example 4 of the present invention. In the said example, sensitivity analysis was conducted using an artificially produced a low rate of microsatellite instability sample and it was identified that this method allowed analysis of microsatellite instability present at a rate of 5%, which could not be analyzed by a conventional method (Pentaplex sequencing).

Accordingly, in another aspect, the present invention provides a method for diagnosing microsatellite instability (MSI), based on detection of base mutations of a target nucleic acid comprising:

(a) purifying the target nucleic acid from a test sample, and mixing the target nucleic acid with a PNA probe selected from the group consisting of sequences having SEQ ID NOS: 11 to 23 and sequences complementary thereto, to hybridize the PNA probe with the target nucleic acid;

(b) denaturating the hybridized product, while changing a temperature, to obtain a melting curve; and (c) analyzing the obtained melting curve to detect a presence of base mutations in a microsatellite marker present in the target nucleic acid and the number of the base mutations, wherein the target nucleic acid comprises BAT25, BAT26, NR21, NR24 or NR27 as the microsatellite marker.

Here, whether or not deletion of microsatellite markers (BAT25, BAT26, NR21, NR24, and NR27) of Quasi loci of target nucleic acids has been occurred can be identified using the diagnostic method.

In the present invention, the test sample may be derived from a specific tissue or organ of animals including humans. Representative examples of such tissue include connective, skin, muscle or nervous tissues. Representative examples of the organ include eyes, brain, lung, liver, spleen, bone marrow, thymus, heart, lymph, blood, bone, cartilage, pancreas, kidney, gallbladder, stomach, small intestine, testis, ovaries, uterus, rectum, nervous systems, glands and blood vessels.

The test sample includes any cell, tissue, fluid, or any other medium that can be effectively analyzed by the present invention, which can be derived from a biological source, and encompasses samples derived from food produced for human and/or animal consumption. In addition, the sample to be analyzed includes a biological fluid and examples thereof include, but are not limited to, sputum, blood, serum, plasma, lymph, milk, urine, feces, intraocular fluid, saliva, semen, brain extract (for example, brain fraction), spinal fluid, tissue extract of appendix, spleen and tonsil.

In the present invention, the PNA probe is designed such that a binding force in perfect match (perfect hybridization) between the PNA probe and a target microsatellite sequence is higher than a polymerase elongation reaction temperature and a binding force in mismatch (hybridization with at least one deletion) between the PNA probe and a target microsatellite sequence is lower than the polymerase elongation reaction temperature.

In the present invention, the PNA probe has an expected melting temperature (Tm) when forming perfect match with a base sequence of the target nucleic acid, and the PNA probe has a lower melting temperature (Tm) than the expected melting temperature (Tm) when forming mismatch with the target nucleic acid having at least one base mutation.

According to the invention, the base mutation includes mutation caused by deletion of 2 to 14 bases of the target nucleic acid.

In the present invention, preferably, the fluorescent PNA probe has a reporter and a quencher at both ends thereof. That is, the reporter and the quencher capable of quenching reporter fluorescence may be coupled to both ends of the PNA probe according to the present invention. The reporter may include one or more selected from the group consisting of FAM (6-carboxyfluorescein), Texas red, HEX (2',4',5',7',-tetrachloro-6-carboxy-4,7-dichlorofluorescein) and CY5, and the quencher may include one or more selected from the group consisting of TAMRA (6-carboxytetramethyl-rhodamine), BHQ1, BHQ2 and Dabcyl, but is not limited thereto. Preferably, Dabcyl is used.

In the present invention, the base mutations of two or more target nucleic acids may be detected using the two or more target nucleic acids and PNA probes labeled with different reporters for respective target nucleic acids. Thus, the method can be used to analyze base mutations of multiple target nucleic acids or single target nucleic acids.

In another aspect, the present invention provides a kit for diagnosis of microsatellite instability (MSI) based on detection of base mutations of a target nucleic acid using melting curve analysis, comprising:

i) a PNA (peptide nucleic acid) probe selected from the group consisting of sequences having SEQ ID NOS: 11 to 23 and sequences complementary thereto; and ii) a primer set selected from the group consisting of: SEQ ID NO: 1 and SEQ ID NO: 2; SEQ ID NO: 3 and SEQ ID NO: 4; SEQ ID NO: 5 and SEQ ID NO: 6; SEQ ID NO: 7 and SEQ ID NO: 8; and SEQ ID NO: 9 and SEQ ID NO: 10, wherein the PNA probe has a reporter and a quencher coupled thereto.

According to the present invention, the PNA probe is designed such that a binding force in perfect match (perfect hybridization) between the PNA probe and a target microsatellite sequence is higher than a polymerase elongation reaction temperature and a binding force in mismatch (hybridization with at least one deletion) between the PNA probe and a target microsatellite sequence is lower than the polymerase elongation reaction temperature.

In the present invention, the PNA probe has an expected melting temperature (Tm) when forming perfect match with a base sequence of the target nucleic acid, and the PNA probe has a lower melting temperature (Tm) than the expected melting temperature (Tm) when forming mismatch with the target nucleic acid with at least one base mutation.

According to the invention, the base mutation includes mutation caused by deletion of 2 to 14 bases of the target nucleic acid.

In the present invention, the kit comprises two or more target nucleic acids and PNA probes labeled with different reporters for the respective target nucleic acids to detect base mutations of the two or more target nucleic acids. Thus, the kit can be used to analyze base mutations of multiple target nucleic acids or single target nucleic acids.

In the present invention, since microsatellite instability (MSI) is caused by malfunction of mismatch repair genes and proofreading genes, the kit can be used for indirect diagnosis of mismatch multiple malfunction or for diagnosis of proofreading malfunction. In addition, since malfunction of mismatch repair genes and proofreading genes results in mutation burden, the kit can be also used for indirect diagnosis of mutational burden (Palmieri, Giuseppe et al., *J. Transl. Med.* 15.1:17, 2017).

Accordingly, in another aspect, the present invention provides a kit for detecting malfunction of genes involved in DNA mismatch repair based on detection of base mutations of a microsatellite target nucleic acid using a PNA (peptide nucleic acid) probe selected from the group consisting of sequences having SEQ ID NOS: 11 to 23 and sequences complementary thereto, wherein the PNA probe has a reporter and a quencher coupled thereto.

In the present invention, the genes involved in the DNA mismatch repair include, but are not limited to, one or more selected from the group consisting of hMLH1 (human MutL homolog 1), hMSH2 (human MutS homolog 2), hMSH3 (human MutS homolog 3), hMSH6 (human MutS homolog 6), hMLH3 (human MutL homolog 3), PMS1 (PMS1 homolog 1), PMS2 (PMS1 homolog 2), EXO1 (exonuclease 1), PCNA (proliferating cell nuclear antigen), RFC (replication factor C), RPA (replication factor A), Pol delta and Ligase1 (DNA ligase 1).

In another aspect, the present invention provides a kit for detecting malfunction of genes involved in DNA proofreading based on detection of base mutations of a microsatellite target nucleic acid using a PNA (peptide nucleic acid) probe selected from the group consisting of sequences having SEQ ID NOS: 11 to 23 and sequences complementary thereto, wherein the PNA probe has a reporter and a quencher coupled.

In the present invention, the genes involved in DNA proofreading preferably include, but are not limited to, one or more selected from the group consisting of POLE (DNA polymerase epsilon) and POLD1 (polymerase delta 1).

In another aspect, the present invention relates to a kit for detecting mutations caused by malfunction of DNA mismatch repair or DNA proofreading using a PNA (peptide nucleic acid) probe selected from the group consisting of sequences having SEQ ID NOS: 11 to 23 and sequences complementary thereto, wherein the PNA probe has a reporter and a quencher coupled.

The kit according to the present invention may optionally include reagents, such as a buffer, a DNA polymerase cofactor and deoxyribonucleotide-5-triphosphate, necessary for performing target amplification PCR reaction (e.g., PCR reaction). In addition, the kit may include various polynucleotide molecules, reverse transcriptase, buffer and reagents, and antibodies for inhibiting DNA polymerase activity. In addition, the optimal amount of the reagent used for a specific reaction in the kit may be readily determined by those skilled in the art who appreciate the disclosure indicated herein. Typically, the kit may be produced as a separate package or compartment containing the aforementioned ingredients.

EXAMPLE

Hereinafter, the present invention will be described in more detail with reference to examples. However, it is obvious to those skilled in the art that these examples are provided only for illustration of the present invention and should not be construed as limiting the scope of the present invention.

Example 1: Production of Primers for Microsatellite Gene Amplification

Base sequences consisting of NR21 (SEQ ID NO: 1 and SEQ ID NO: 2), NR24 (SEQ ID NO: 3 and SEQ ID NO: 4), BAT26 (SEQ ID NO: 5 and SEQ ID NO: 6), NR27 (SEQ ID NO: 7 and SEQ ID NO: 8), and BAT25 (SEQ ID NO: 9 and SEQ ID NO: 10) (Table 1) were produced and used as primers for the polymerase chain reaction of five microsatellite markers of Quasi loci (NR21, NR24, BAT26, NR27 and BAT25).

TABLE 1

| Microsatellite | SEQ ID NO | Name | Base sequence (5'-3') |
|---|---|---|---|
| NR21 | 1 | NR21_F | ATATTTAAATGTATGTCTCC |
|  | 2 | NR21_R | CTGGTCACTCGCGTTTACAA |
| NR24 | 3 | NR24_F | GCTGAATTTTACCTCCTGAC |
|  | 4 | NR24_R | ATTGTGCCATTGCATTCCAA |
| BAT26 | 5 | BAT26_F | GATATTGCAGCAGTCAGAGC |
|  | 6 | BAT26_R | GCTTCTTCAGTATATGTCAATG |
| NR27 | 7 | NR27_F | AACCATGCTTGCAAACCACT |
|  | 8 | NR27_R | CGATAATACTAGCAATGACC |
| BAT25 | 9 | BAT25_F | CTCGCCTCCAAGAATGTAAGT |
|  | 10 | BAT25_R | GTTACCACACTTCAAAATGACA |

Example 2: Production of Bifunctional Fluorescent PNA Probes

Bifunctional fluorescent PNA probes having both a microsatellite instability (MSI) preferential amplification function and a melting temperature analysis function were produced such that the hybridization (match) temperature with the microsatellite stability sequence was higher than the polymerase extension reaction temperature and the hybridization temperature with the microsatellite instability sequence was lower than the polymerase extension reaction temperature. Then, a fluorescent marker and a quencher were coupled to the end of each probe to measure a separating temperature after hybridization. Each bifunctional fluorescent PNA probe was produced to include a single base repeat sequence of microsatellite in the middle thereof and 3 to 8 specific sequences at each end thereof, thereby securing specificity (Table 2).

TABLE 2

| Microsatellite | SEQ ID NO | Name | Base sequence (5'-3') | Fluorescence |
|---|---|---|---|---|
| NR21 | 11 | NR21_1 | Dabcyl-TTGCTAAAAAAAAAAAAAAAAAAAAAAGGC-O-K | (FAM) |
|  | 12 | NR21_2 | Dabcyl-TGTTGCTAAAAAAAAAAAAAAAAAAAAAGGCCA-O-K | (Texas Red) |
|  | 13 | NR21_3 | Dabcyl-GTGTTGCTAAAAAAAAAAAAAAAAAAAAGGCCAG-O-K | (Texas Red) |
| NR24 | 14 | NR24_1 | Dabcyl-CTCACAAAAAAAAAAAAAAAAAAAAATAGGA-O-K | (HEX) |
|  | 15 | NR24_2 | Dabcyl-GTCTCACAAAAAAAAAAAAAAAAAAAATAGGAC-O-K | (HEX) |
|  | 16 | NR24_3 | Dabcyl-CGTCTCACAAAAAAAAAAAAAAAAAAATAGGACT-O-K | (HEX) |
| BAT26 | 17 | BAT26_1 | Dabcyl-GGTAAAAAAAAAAAAAAAAAAAAAGGG-O-K | (FAM) |
| BAT25 | 18 | BAT25_1 | Dabcyl-CTCAAAAAAAAAAAAAAAAAAAAATCA-O-K | (FAM) |
|  | 19 | BAT25_2 | Dabcyl-TCTCAAAAAAAAAAAAAAAAAAAATCAA-O-K | (FAM) |
|  | 20 | BAT25_3 | Dabcyl-TTCTCAAAAAAAAAAAAAAAAAAATCAAA-O-K | (HEX) |
|  | 21 | BAT25_4 | Dabcyl-GTTCTCAAAAAAAAAAAAAAAAAATCAAAA-O-K | (HEX) |
| NR27 | 22 | NR27_1 | Dabcyl-TGGTAAAAAAAAAAAAAAAAAAAAGCC-O-K | (FAM) |
|  | 23 | NR27_2 | Dabcyl-GGTAAAAAAAAAAAAAAAAAAAAAGCC-O-K | (FAM) |

*In Table 2, O-represents a linker and K represents lysine.

Example 3: Verification of Bifunctional PNA Probe-Based MSI Discrimination Kit Using Standard Cell Lines PCR was performed with a CFX96™ Real-Time system (BIO-RAD, USA) using the standard cell lines of microsatellite instability (MSI) and microsatellite stability (MSS) (Table 3), the primers produced in Example 1 and the bifunctional PNA fluorescent probes produced in Example 2 (Table 3).

TABLE 3

| # | Cell line | Microsatellite status |
|---|---|---|
| 1 | CS174T | MSI |
| 2 | DLD | MSI |
| 3 | HCT8 | MSI |
| 4 | HCT116 | MSI |
| 5 | NCC59 | MSI |
| 6 | PKO | MSI |
| 7 | SNU1 | MSI |
| 8 | SNU638 | MSI |
| 9 | SNU1544 | MSI |
| 10 | SW48 | MSI |
| 11 | Colo205 | MSS |
| 12 | Hela | MSS |
| 13 | MCF7 | MSS |
| 14 | PC9 | MSS |
| 15 | SNU601 | MSS |

Figure 1:
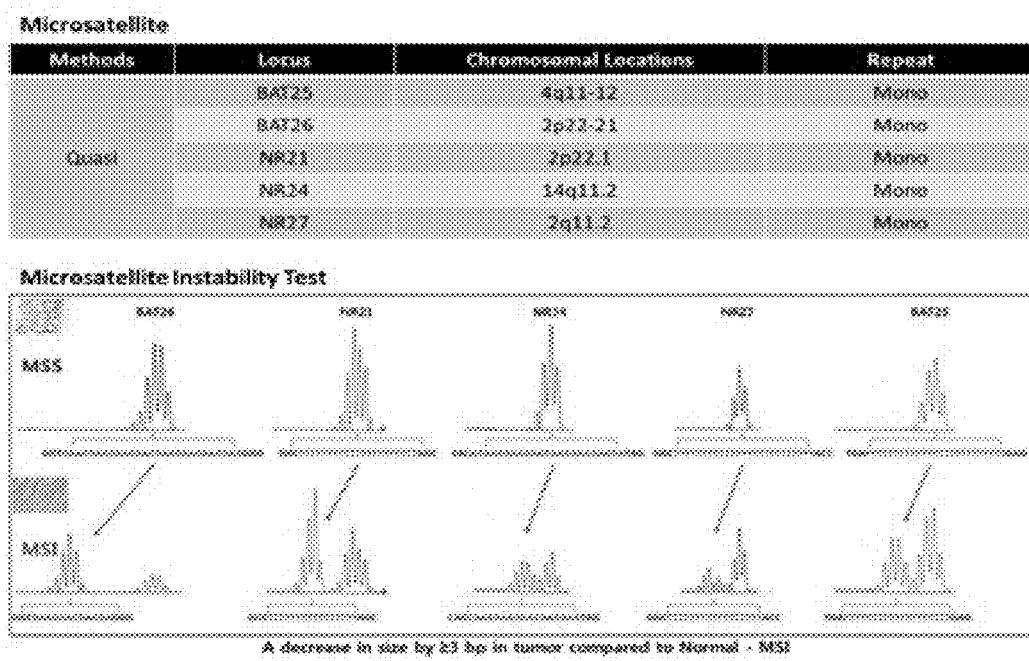
FIG. 1 shows target microsatellites (BAT25, BAT26, NR21, NR24, and NR27) and results of conventional analysis methods.
Figure 2:
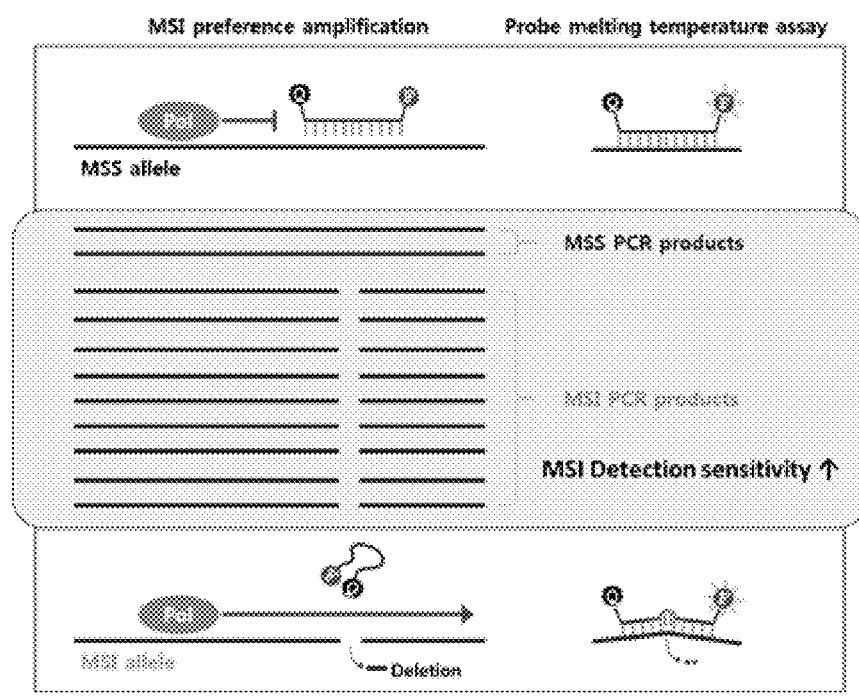
FIG. 2 is a schematic diagram showing analysis on deletion of microsatellites with high sensitivity using a bifunctional PNA probe.
Figure 3:
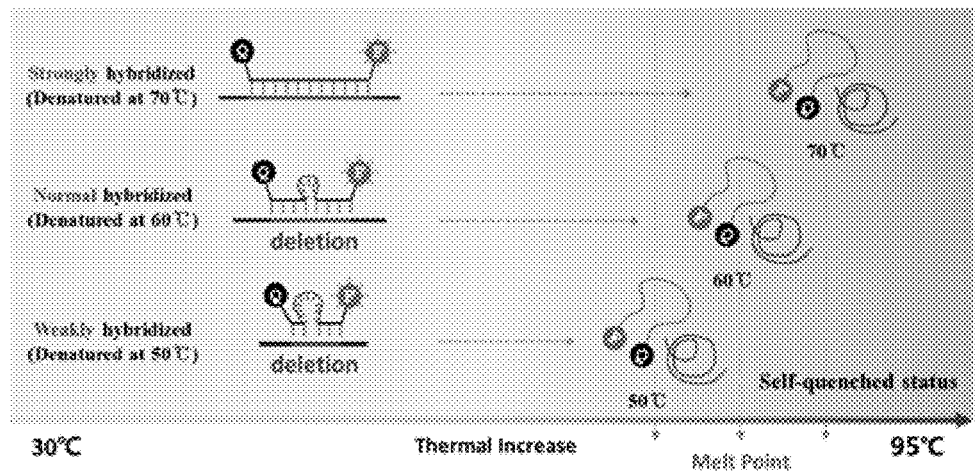
FIG. 3 is a schematic diagram illustrating a step of hybridization and a step of obtaining a melting curve to identify the presence of base deletion of microsatellites using a fluorescent PNA probe.

Real-time polymerase chain reaction (PCR) used herein was asymmetric PCR to produce single-stranded target nucleic acids. The conditions of the asymmetric PCR are as follows: 1 µl of standard cell line DNA (Table 3) was added to 2× SeaSunBio Real-Time FMCA™ buffer (SeaSunBio, Korea), 2.5 mM $MgCl_2$, 200 µM dNTPs, 1.0 U Taq polymerase, 0.05 µM forward primer (Table 1) and 0.5 µM reverse primer (Table 1, asymmetric PCR), such that the total volume was adjusted to 20 µl, real-time PCR was performed, 0.5 µl of the fluorescent PNA probe (Table 2) was added thereto and then melting curve analysis was performed. The schematic views of the test method are shown in FIGS. 2 and 3, and analysis was carried out under the conditions shown in FIG. 4.

Figure 5:
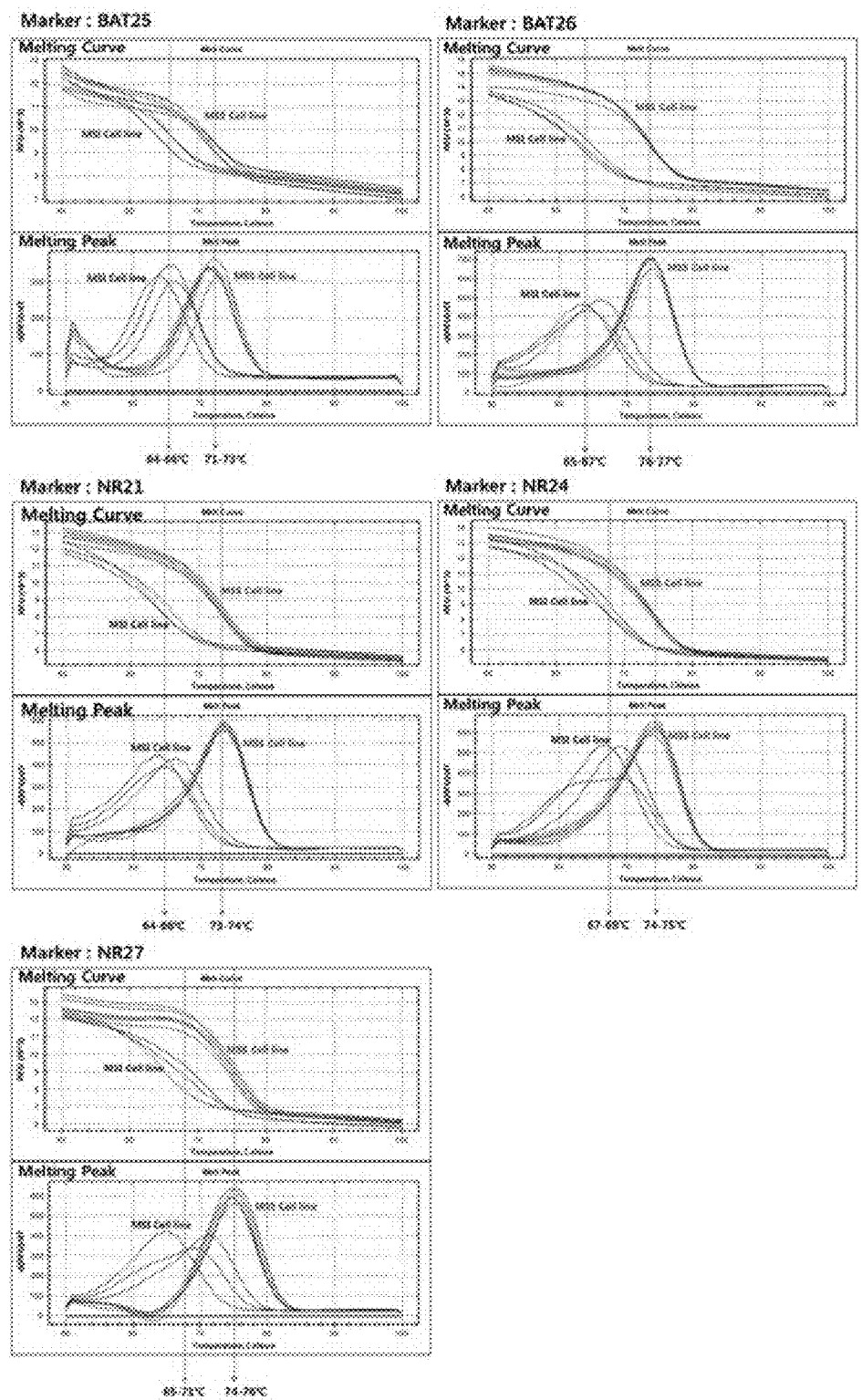
FIG. 5 shows results of analysis on the number and genotypes of deleted base mutations by a single analysis method using MSI and MSS cell lines for five microsatellites (BAT25, BAT26, NR21, NR24, and NR27) of Quasi loci.

As a result, as can be seen from FIG. 5, the binding temperature of the PNA probe targeting NR21, NR24, BAT26, NR27 and BAT25 as microsatellite markers in the MSI cell line was lower than the binding temperature in the case of the MSS standard cell line.

Example 4: Comparative Analysis on Sensitivity of Bifunctional PNA Probes-Based MSI Discrimination Kit The DNAs extracted from the microsatellite instability (MSI) standard cell lines (Table 3) were mixed at ratios of 5, 10, 20, 40 and 100% with microsatellite stability (MSS) standard cell lines, the resulting mixtures were used as samples for sensitivity analysis, and PCR was performed on the CFX96™ Real-Time system (BIO-RAD, USA) using the primers and the bifunctional PNA fluorescent probes produced in Examples 1 and 2.

Real-time polymerase chain reaction (PCR) used herein was asymmetric PCR to produce single-stranded target nucleic acids. The conditions of the asymmetric PCR were as follows; 1 µl of standard cell line DNA (Table 3) was added to 2× SeaSunBio Real-Time FMCA™ buffer (SeaSunBio, Korea), 2.5 mM $MgCl_2$, 200 µM dNTPs, 1.0 U Taq polymerase, 0.05 µM forward primer (Table 1) and 0.5 µM reverse primer (Table 1, asymmetric PCR), such that the total volume was adjusted to 20 µl, real-time PCR was performed, 0.5 µl of the fluorescent PNA probe (Table 2) was added thereto and then melting curve analysis was performed. The schematic views of the test method are shown in FIGS. 2 and 3, and analysis was carried out under the conditions shown in FIG. 4.

Figures 6, 7:
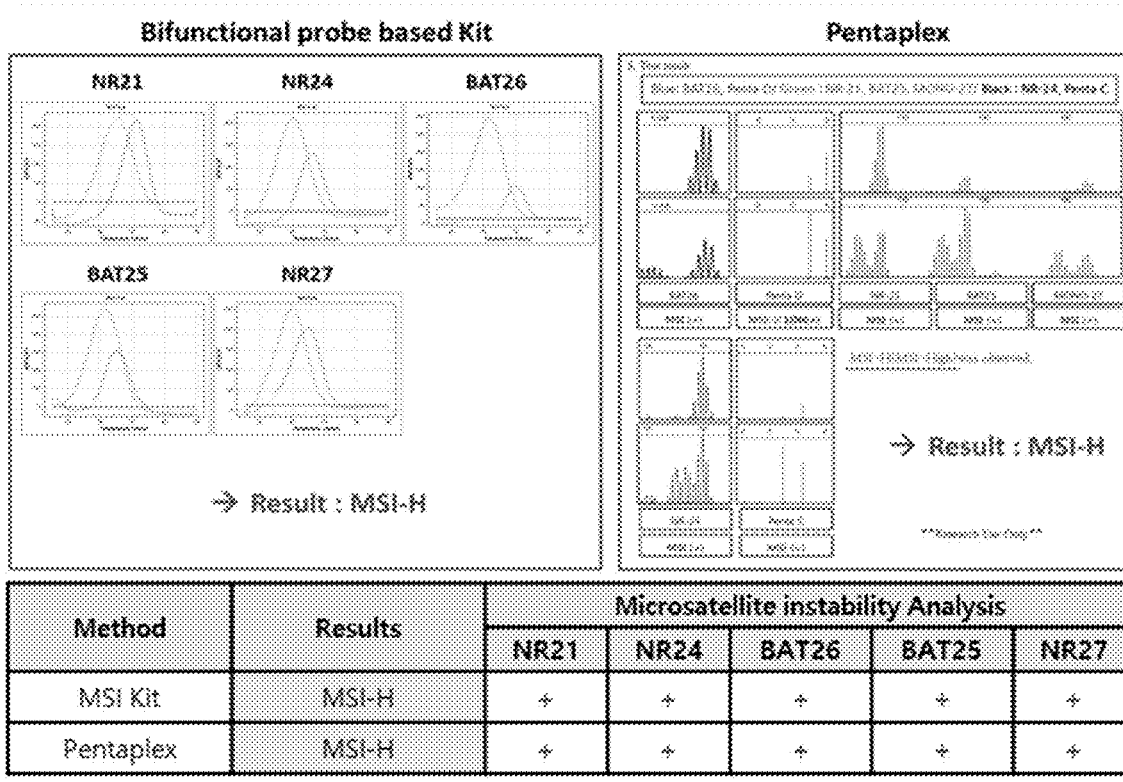
FIG. 6 is a graph showing results of sensitivity analysis using a highly sensitive kit for diagnosing microsatellite deletion, as compared with a conventional analysis method, wherein the result represents microsatellite instability (MSI-high).
FIG. 7 is a graph showing results of colorectal cancer sample analysis using a highly sensitive kit for diagnosing microsatellite deletion, as compared with a conventional analysis method, wherein the result represents microsatellite instability (MSI-high).

Results of the analysis showed that it is possible to analyze instability of microsatellite mixed at 5% and 10%, which could not be detected by the conventional pentaplex method (FIG. 6).

Example 5: Verification of Bifunctional PNA Probe-Based MSI Discrimination Kit Using Clinical Samples DNAs were extracted from clinical tissues considered to develop colon cancer and stomach cancer, and the surrounding normal tissues, and PCR was then performed on CFX96™ real-time system (BIO-RAD, USA) using the primers and bifunctional PNA fluorescent probes produced in Examples 1 and 2.

Real-time polymerase chain reaction (PCR) used herein was asymmetric PCR to produce single-stranded target nucleic acids. The conditions of the asymmetric PCR were as follows; 1 µl of standard cell line DNA (Table 3) was added to 2× SeaSunBio Real-Time FMCA™ buffer (SeaSunBio, Korea), 2.5 mM $MgCl_2$, 200 µM dNTPs, 1.0 U Taq polymerase, 0.05 µM forward primer (Table 1) and 0.5 µM reverse primer (Table 1, asymmetric PCR), such that the total volume was adjusted to 20 µl, real-time PCR was performed, 0.5 µl of the fluorescent PNA probe (Table 2) was added thereto and then melting curve analysis was performed. The schematic views of the test method are shown in FIGS. 2 and 3, and analysis was carried out under the conditions shown in FIG. 4.

Whether or not instability of microsatellite marker genes was present was comparatively analyzed by comparing the melting temperature between the cancer tissues and the surrounding normal tissues. Final results of the method according to the present invention were compared with those of the Petaplex method, which is a conventional MSI analysis method.

Figure 8:
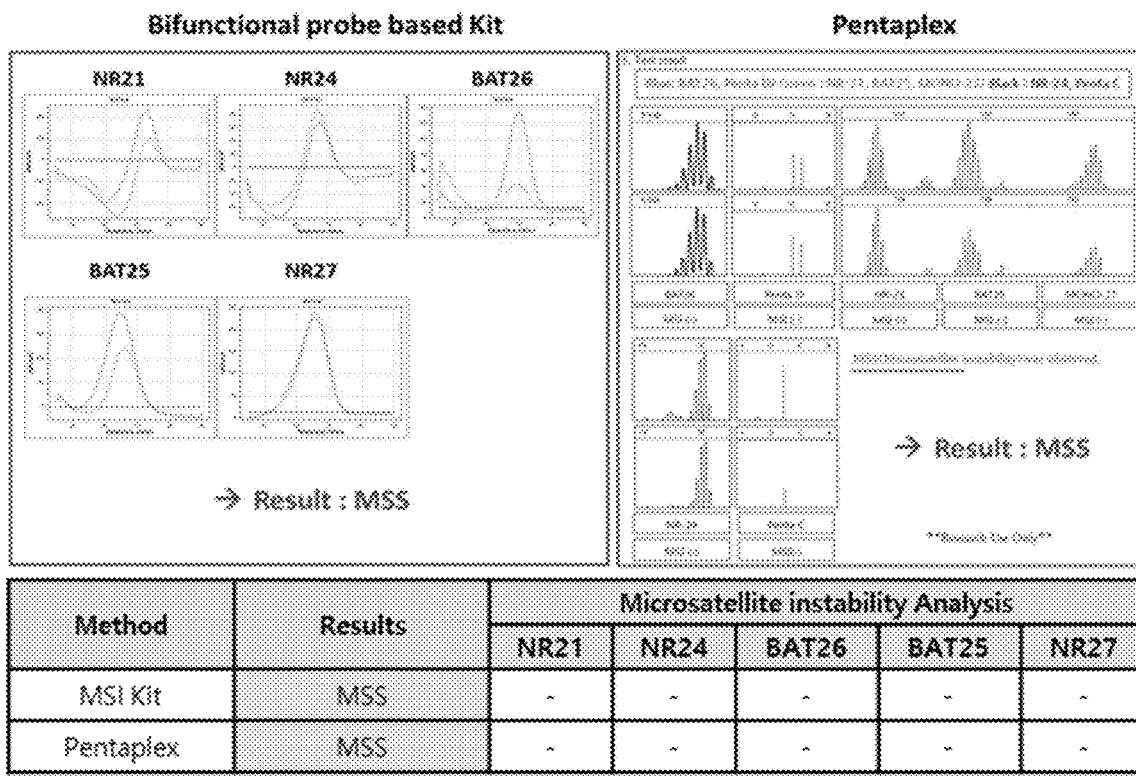
FIG. 8 is a graph showing results of colorectal cancer sample analysis using a highly sensitive kit for diagnosing microsatellite deletion, as compared with a conventional analysis method, wherein the result represents microsatellite stability (MSS).
Figure 9:
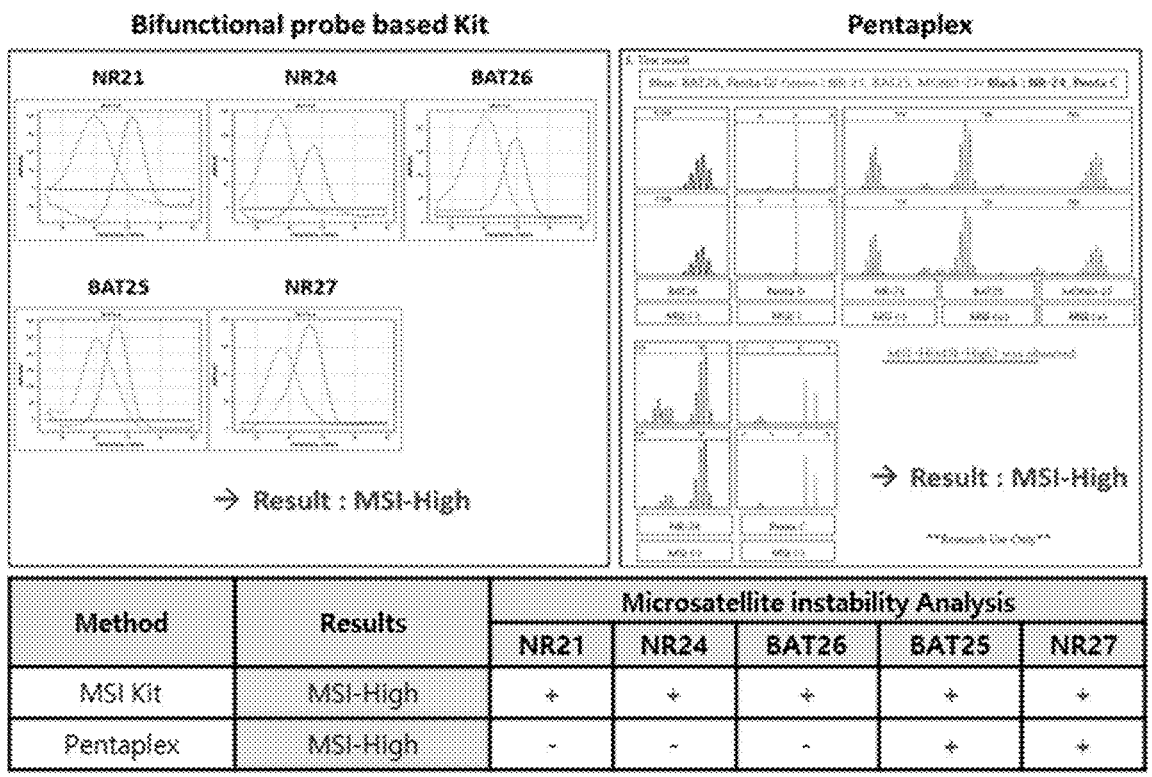
FIG. 9 is a graph showing results of stomach cancer sample analysis using a highly sensitive kit for diagnosing microsatellite deletion, as compared with a conventional analysis method, wherein the result represents microsatellite instability (MSI-High).
Figure 10:
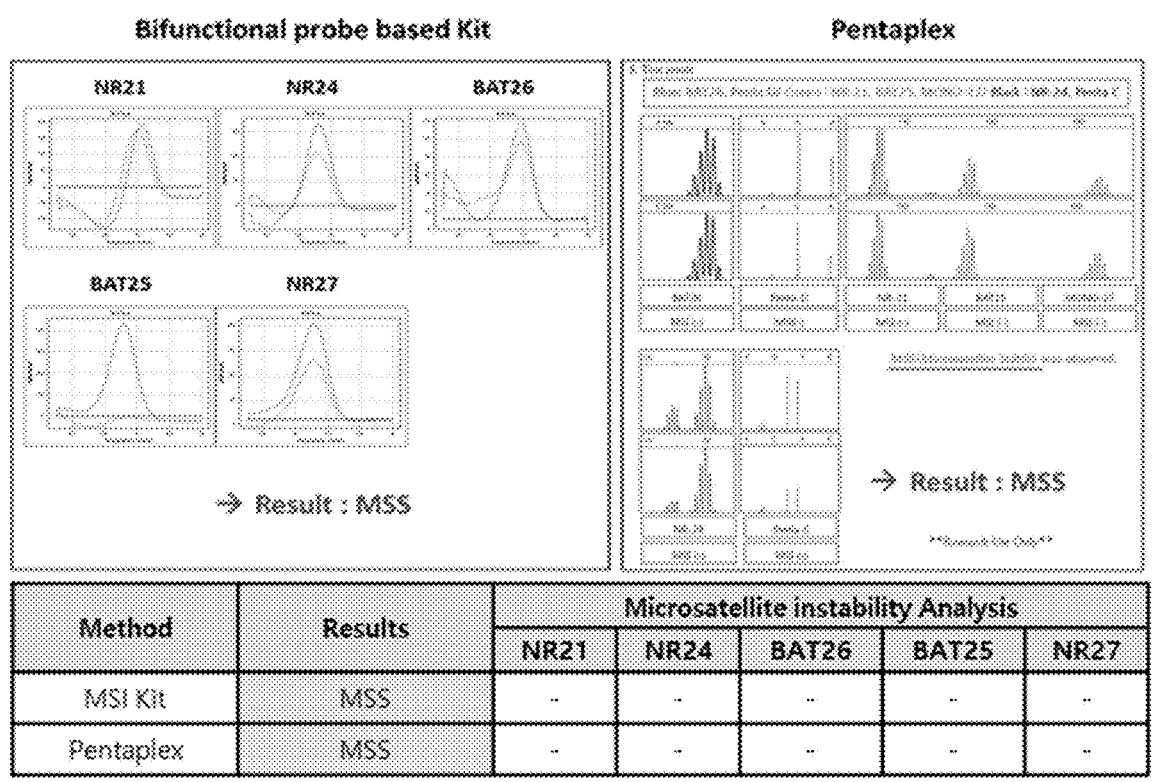
FIG. 10 is a graph showing results of stomach cancer sample analysis using a highly sensitive kit for diagnosing microsatellite deletion, as compared with a conventional analysis method, wherein the result represents microsatellite stability (MSS).

As can be seen from FIG. 7, analysis using bifunctional PNA fluorescent probes showed the same results of "MSI-high" in clinical tissues which indicated "MSI-high" (wherein deletion of two or more marker genes among five microsatellite genes is confirmed to be present) in analysis using the conventional pentaplex method. In addition, as shown in FIG. 8, analysis using the bifunctional PNA fluorescent probe targeting colorectal cancer, which showed "MSS" in the conventional analysis, showed the same result as "MSS". The results of analysis on clinical tissues considered to develop stomach cancer, and the surrounding normal tissues, were also the same as above (FIGS. 9 and 10).

In addition, further comparative analysis with the pentaplex method was conducted on a number of clinical tissues. As a result, it could be seen that results of analysis using the conventional pentaplex method correspond to those using the bifunctional fluorescent PNA probes.

INDUSTRIAL APPLICABILITY

The present invention relates to a method and kit for diagnosing microsatellite instability (MSI) based on analysis on the number of base mutations using a bifunctional PNA probe including a reporter and a quencher coupled thereto, which can analyze the presence of deletion of microsatellite marker genes with high sensitivity and specificity using five microsatellite markers of Quasi loci and thus has advantages of reducing costs, shortening a test time, and the like, as compared to conventional MSI diagnostic methods.

Although specific configurations of the present invention has been described in detail, those skilled in the art will appreciate that this description is provided as preferred embodiments for illustrative purposes and should not be construed as limiting the scope of the present invention. Therefore, the substantial scope of the present invention is defined by the accompanying claims and equivalents thereto.

The invention claimed is:

1. A method for diagnosing microsatellite instability (MSI), based on detection of base mutations of a target nucleic acid comprising:
   (a) purifying the target nucleic acid from a test sample, and mixing the target nucleic acid with a PNA probe in which the nucleotide sequence consists of SEQ ID NO: 19 or the complement thereof, to hybridize the PNA probe with the target nucleic acid;
   (b) denaturating the hybridized product, while changing a temperature, to obtain a melting curve; and
   (c) analyzing the obtained melting curve to detect a presence of base mutations in a microsatellite marker present in the target nucleic acid and the number of the base mutations, wherein the target nucleic acid comprises BAT25 as the microsatellite marker.

2. The method according to claim 1, wherein the PNA probe has an expected melting temperature (Tm) when forming perfect match with a base sequence of the target nucleic acid, and the PNA probe has a lower melting temperature (Tm) than the expected melting temperature (Tm) when forming mismatch with the target nucleic acid having at least one base mutation.

3. The method according to claim 1, wherein the base mutations are caused by deletion of 2 to 14 bases of the target nucleic acid.

4. The method according to claim 1,
   wherein the PNA probe has a reporter and a quencher coupled thereto, and
   wherein the reporter comprises one or more selected from the group consisting of FAM (6-carboxyfluorescein), Texas red, HEX (2',4',5',7',-tetrachloro-6-carboxy-4,7-dichlorofluorescein) and CY5.

5. The method according to claim 1,
   wherein the PNA probe has a reporter and a quencher coupled thereto, and
   wherein the quencher comprises one or more selected from the group consisting of TAMRA (6-carboxytetramethyl-rhodamine), BHQ1, BHQ2 and Dabcyl.

6. The method according to claim 1, wherein base mutations of two or more target nucleic acids are detected using the two or more target nucleic acids and PNA probes labeled with different reporters for respective target nucleic acids.

7. The method according to claim 1, wherein the PNA probe has a reporter and a quencher coupled thereto.

* * * * *

SEQUENCE LISTING

<160> NUMBER OF SEQ ID NOS: 23

<210> SEQ ID NO 1
<211> LENGTH: 20

```
<212> TYPE: DNA
<213> ORGANISM: Artificial Sequence
<220> FEATURE:
<223> OTHER INFORMATION: NR21_F

<400> SEQUENCE: 1
atatttaaat gtatgtctcc                                           20

<210> SEQ ID NO 2
<211> LENGTH: 20
<212> TYPE: DNA
<213> ORGANISM: Artificial Sequence
<220> FEATURE:
<223> OTHER INFORMATION: NR21_R

<400> SEQUENCE: 2
ctggtcactc gcgtttacaa                                           20

<210> SEQ ID NO 3
<211> LENGTH: 20
<212> TYPE: DNA
<213> ORGANISM: Artificial Sequence
<220> FEATURE:
<223> OTHER INFORMATION: NR24_F

<400> SEQUENCE: 3
gctgaatttt acctcctgac                                           20

<210> SEQ ID NO 4
<211> LENGTH: 20
<212> TYPE: DNA
<213> ORGANISM: Artificial Sequence
<220> FEATURE:
<223> OTHER INFORMATION: NR24_R

<400> SEQUENCE: 4
attgtgccat tgcattccaa                                           20

<210> SEQ ID NO 5
<211> LENGTH: 20
<212> TYPE: DNA
<213> ORGANISM: Artificial Sequence
<220> FEATURE:
<223> OTHER INFORMATION: BAT26_F

<400> SEQUENCE: 5
gatattgcag cagtcagagc                                           20

<210> SEQ ID NO 6
<211> LENGTH: 22
<212> TYPE: DNA
<213> ORGANISM: Artificial Sequence
<220> FEATURE:
<223> OTHER INFORMATION: BAT26_R

<400> SEQUENCE: 6
gcttcttcag tatatgtcaa tg                                        22

<210> SEQ ID NO 7
<211> LENGTH: 20
<212> TYPE: DNA
<213> ORGANISM: Artificial Sequence
<220> FEATURE:
<223> OTHER INFORMATION: NR27_F

<400> SEQUENCE: 7
```

```
aaccatgctt gcaaaccact                                          20

<210> SEQ ID NO 8
<211> LENGTH: 20
<212> TYPE: DNA
<213> ORGANISM: Artificial Sequence
<220> FEATURE:
<223> OTHER INFORMATION: NR27_R

<400> SEQUENCE: 8
cgataatact agcaatgacc                                          20

<210> SEQ ID NO 9
<211> LENGTH: 21
<212> TYPE: DNA
<213> ORGANISM: Artificial Sequence
<220> FEATURE:
<223> OTHER INFORMATION: BAT25_F

<400> SEQUENCE: 9
ctcgcctcca agaatgtaag t                                        21

<210> SEQ ID NO 10
<211> LENGTH: 22
<212> TYPE: DNA
<213> ORGANISM: Artificial Sequence
<220> FEATURE:
<223> OTHER INFORMATION: BAT25_R

<400> SEQUENCE: 10
gttaccacac ttcaaaatga ca                                       22

<210> SEQ ID NO 11
<211> LENGTH: 29
<212> TYPE: DNA
<213> ORGANISM: Artificial Sequence
<220> FEATURE:
<223> OTHER INFORMATION: NR21_1

<400> SEQUENCE: 11
ttgctaaaaa aaaaaaaaaa aaaaaaggc                                29

<210> SEQ ID NO 12
<211> LENGTH: 33
<212> TYPE: DNA
<213> ORGANISM: Artificial Sequence
<220> FEATURE:
<223> OTHER INFORMATION: NR21_2

<400> SEQUENCE: 12
tgttgctaaa aaaaaaaaaa aaaaaaaagg cca                           33

<210> SEQ ID NO 13
<211> LENGTH: 35
<212> TYPE: DNA
<213> ORGANISM: Artificial Sequence
<220> FEATURE:
<223> OTHER INFORMATION: NR21_3

<400> SEQUENCE: 13
gtgttgctaa aaaaaaaaaa aaaaaaaaag gccag                         35

<210> SEQ ID NO 14
<211> LENGTH: 34
<212> TYPE: DNA
<213> ORGANISM: Artificial Sequence
```

```
<220> FEATURE:
<223> OTHER INFORMATION: NR24_1

<400> SEQUENCE: 14
ctcacaaaaa aaaaaaaaaa aaaaaaaaat agga                          34

<210> SEQ ID NO 15
<211> LENGTH: 37
<212> TYPE: DNA
<213> ORGANISM: Artificial Sequence
<220> FEATURE:
<223> OTHER INFORMATION: NR24_2

<400> SEQUENCE: 15
gtctcacaaa aaaaaaaaaa aaaaaaaaaa ataggac                       37

<210> SEQ ID NO 16
<211> LENGTH: 39
<212> TYPE: DNA
<213> ORGANISM: Artificial Sequence
<220> FEATURE:
<223> OTHER INFORMATION: NR24_3

<400> SEQUENCE: 16
cgtctcacaa aaaaaaaaaa aaaaaaaaaa aataggact                     39

<210> SEQ ID NO 17
<211> LENGTH: 32
<212> TYPE: DNA
<213> ORGANISM: Artificial Sequence
<220> FEATURE:
<223> OTHER INFORMATION: BAT26_1

<400> SEQUENCE: 17
ggtaaaaaaa aaaaaaaaaa aaaaaaaaag gg                            32

<210> SEQ ID NO 18
<211> LENGTH: 31
<212> TYPE: DNA
<213> ORGANISM: Artificial Sequence
<220> FEATURE:
<223> OTHER INFORMATION: BAT25_1

<400> SEQUENCE: 18
ctcaaaaaaa aaaaaaaaaa aaaaaaaatc a                             31

<210> SEQ ID NO 19
<211> LENGTH: 33
<212> TYPE: DNA
<213> ORGANISM: Artificial Sequence
<220> FEATURE:
<223> OTHER INFORMATION: BAT25_2

<400> SEQUENCE: 19
tctcaaaaaa aaaaaaaaaa aaaaaaaaat caa                           33

<210> SEQ ID NO 20
<211> LENGTH: 35
<212> TYPE: DNA
<213> ORGANISM: Artificial Sequence
<220> FEATURE:
<223> OTHER INFORMATION: BAT25_3

<400> SEQUENCE: 20
ttctcaaaaa aaaaaaaaaa aaaaaaaaaa tcaaa                         35
```

```
<210> SEQ ID NO 21
<211> LENGTH: 37
<212> TYPE: DNA
<213> ORGANISM: Artificial Sequence
<220> FEATURE:
<223> OTHER INFORMATION: BAT25_4

<400> SEQUENCE: 21
gttctcaaaa aaaaaaaaaa aaaaaaaaaa atcaaaa                               37

<210> SEQ ID NO 22
<211> LENGTH: 34
<212> TYPE: DNA
<213> ORGANISM: Artificial Sequence
<220> FEATURE:
<223> OTHER INFORMATION: NR27_1

<400> SEQUENCE: 22
tggtaaaaaa aaaaaaaaaa aaaaaaaaaa agcc                                  34

<210> SEQ ID NO 23
<211> LENGTH: 33
<212> TYPE: DNA
<213> ORGANISM: Artificial Sequence
<220> FEATURE:
<223> OTHER INFORMATION: NR27_2

<400> SEQUENCE: 23
ggtaaaaaaa aaaaaaaaaa aaaaaaaaaa gcc                                   33
```